United States Patent [19]
Metzler et al.

[11] Patent Number: 6,162,633
[45] Date of Patent: Dec. 19, 2000

[54] PROCESS AND KIT FOR FRAGMENT CLONING

[76] Inventors: Thomas Metzler, Maistr. 57, D-80337 München; Harald Sobek; Rolf Reichhuber, both of Am Burgholz 4a, D-82377 Penzberg, all of Germany

[21] Appl. No.: 09/193,488

[22] Filed: Nov. 17, 1998

[30] Foreign Application Priority Data

Nov. 17, 1997 [EP] European Pat. Off. ............ 97 120 089

[51] Int. Cl.⁷ ....................................................... C12N 1/20
[52] U.S. Cl. .................... 435/252.33; 435/243; 435/260; 435/320.1
[58] Field of Search ................................ 435/320.1, 69.1, 435/70.1, 71.1, 325, 243, 252.1, 252.3, 252.33, 471, 472, 474, 260, 257.2; 536/23.1

[56] References Cited

FOREIGN PATENT DOCUMENTS 0 620 280 A1 10/1994 European Pat. Off. .

OTHER PUBLICATIONS

Methods In Enzymology 68, pp. 309–327, John Collins, Dec. 1979.

Hohn, B., and Collins, J. 1980, "A small cosmid for efficient cloning of large DNA fragments," Gene 11: 291–298.

Friedman, A.M. et al., 1982, "Construction of a broad host range cosmid cloning vector and its use in the genetic analysis of Rhizobium mutants," Gene 18: 289–296.

Knauf, V.C., and Nester, E.W. 1982, "Wide Host Range Cloning Vectors: A Cosmid Clone Bank of an Agrobacterium Ti Plasmid," Plasmid 8: 45–54.

Saito, I., and Stark, G.R. 1986, "Charomids: Cosmid vectors for efficient cloning and mapping of large or small restriction fragments," Proc. Natl. Acad. Sci. USA 83: 8664–8668.

*Primary Examiner*—Remy Yucel
*Attorney, Agent, or Firm*—Victor K. Lee; Douglas A. Petry

[57] ABSTRACT

The subject matter of the invention concerns three cosmid vectors which are suitable for fragment cloning of a size between 7 and 36 kb. These vectors consist of an *E. coli* ColE1 replica, an ampicillin resistance gene, a multiple cloning cassette, cos sites for in vitro packaging with the lambda packaging extracts as well as fragments from the genome of the bacteriophage lambda. The lambda sequences were selected in a way to prevent lytic processes, vector instabilities (deletions) and unwanted recombination events between lambda DNA and the fragment to be cloned. Depending on the length of the lambda fragment inserted in the corresponding vector heterologous fragments of different lengths can be cloned.

8 Claims, 4 Drawing Sheets

SEQUENCE LISTING

```
<160> NUMBER OF SEQ ID NOS: 3

<210> SEQ ID NO 1
<211> LENGTH: 129
<212> TYPE: DNA
<213> ORGANISM: Artificial Sequence
<220> FEATURE:
<223> OTHER INFORMATION: Description of Artificial Sequence:  Cloning
      cassete

<400> SEQUENCE: 1
caggaaacag ctatgactaa tacgactcac tatagggaga gcggccgcat ttaaatggcc        60
atataggccc ccgggactag tgcggccgcg tattctatag tgtcacctaa atactggccg       120
tcgttttac                                                               129

<210> SEQ ID NO 2
<211> LENGTH: 24
<212> TYPE: DNA
<213> ORGANISM: Homo sapiens

<400> SEQUENCE: 2
cacaagggct actggttgcc gatt                                               24

<210> SEQ ID NO 3
<211> LENGTH: 22
<212> TYPE: DNA
<213> ORGANISM: Homo sapiens

<400> SEQUENCE: 3
agcttcccaa cgtgatcgcc tt                                                 22
```

PROCESS AND KIT FOR FRAGMENT CLONING

The present application claims priority to European Patent Application No. 97 120 089.4, filed Nov. 17, 1997.

BACKGROUND OF THE INVENTION

1. Field of the Invention

The invention concerns a process and kit for cloning of DNA fragments as for example PCR amplification products which cannot be cloned with plasmids because of their size and which are too small to be cloned in cosmids. For this purpose modified cosmid vectors were constructed which are suitable for cloning of DNA amplification products and DNA fragments of a certain size.

2. Description of Related Art

Several state of the art methods for cloning of heterologous DNA are known. The simplest method is the use of plasmid vectors which contain a suitable replication origin, an antibiotic resistance gene as a selection marker as well as at least one suitable restriction site. If heterologous DNA fragments exceeding 10 kb are however inserted in conventional plasmids such as pUC or other pBR derivatives this may lead to structures which cannot, as experience has shown, be cloned without deletions in recombination deficient host cells. The disadvantage of this method is the fact that only DNA fragments of a limited maximum size of approximately 10 kb can be cloned efficiently.

Cloning of larger fragments is, according to the state of the art, performed with vectors and based on the reproduction cycle of the bacteriophage lambda. Here, the lambda DNA present in a linear form is prepared first. Then an internal fragment, the so-called stuffer, is removed with a suitable restriction enzyme digestion. The DNA to be cloned is inserted instead of the stuffer between the vector arms (e.g. lambda-gt10; lambda-gt11) by one ligation step. Subsequently, the resulting DNA is incubated with a phage particle extract which was prepared before. With this so-called in vitro packaging reaction infectious phage particles are produced which can be used for infecting appropriate host bacteria. With this method fragments of up to 20 kb can be cloned (Winnacker, E.-L., In: From Genes to Clones, VCH Weinheim (1987) Winnacker, E.-L (ed), pp 154–167); Rimm, D. L. et al. (1980), Gene 12, 301–309).

The disadvantage of this method is the fact that the DNA cloned as described above always remains inserted in the genome of the lambda phage. The lambda genome itself contains genes that code for lytic functions and thus lead to lysis of the bacteria cells so that the so-called plaques are continuously formed because of a certain infection. Compared to the reproduction and preparation of plasmids the reproduction and preparation of lambda DNA is therefore much more cost- and time-intensive. For this reason lambda vectors are, in practice, only used for gene banks but not for cloning of special DNA fragments.

Furthermore, cosmid vectors suitable for cloning of particularly large DNA fragments are known. These are plasmids which additionally contain a cos region. This cos region is derived from the terminal sequences of the genome of the bacteriophage lambda and has an important function in its reproduction cycle: during the replication of the DNA phage concatamers are produced. They are multimers of the phage genome which are arranged in the form of a tandem. During the packaging reaction the concatamers are split at the cos regions by the A-protein of the lambda phage. From this result single linear phage genomes with cohesive ends which are subsequently packed in phage particles.

The DNA fragments to be cloned and the linearized cosmid vectors are ligated under conditions that would in vitro lead to multimer concatamers. By incubation with a packaging extract monomer molecules result from the concatamers which contain each the fragment to be cloned between 2 cos regions and which are consequently packed in the phage particles of the extract. Subsequently, an infection (also called transduction) in suitable host bacteria is performed. Circular cosmids are produced in the host by the cohesive ends (resulting from the cleavage of the cos regions by the protein A as described above) of the terminal cos sequences. These cosmids contain the fragment to be cloned and can be easily reproduced and prepared due to their plasmid characteristics.

Usual cosmids have a size ranging from 4 to 6 kb since for gene banks the fragments to be cloned must be as large as possible (Maniatis et. al. Molecular Cloning. A Laboratory Manual, Cold Spring Harbour, Laboratory Press, Cold Spring Harbour, N.Y., 1982, p. 45). The size of the fragments to be cloned depends on the size of the cosmid used: with the help of the lambda packaging system DNA molecules of a size ranging from 38 kb to 52 kb are packed. Fragments of this size less the size of the cosmid used can therefore be cloned very efficiently. If a cosmid like for example pHC79 (Hohn and Collins (1980), Gene 11, pp. 291–298) has a size of 6.5 kb fragments from 31.5–45.5 kb can be cloned.

The disadvantage of the cosmids is that only DNA fragments of a certain size can be inserted. There is therefore no state of the art method enabling in a simple way the cloning of fragments that are on the one hand too small for packaging of cosmid vectors and on the other hand too big for cloning with plasmids (without cos regions for in vitro packaging).

Fragments of this size category are produced by PCR amplification reactions for example with the "Expand" Long Template PCR System (Boehringer Mannheim catalogue No. 1681834). This kit contains reagents for a PCR method allowing the amplification of genomic fragments of a maximum size of approximately 30 kb. Before this invention was made direct cloning of the relevant amplification products had however not been possible with the plasmid and cosmid vectors known from the state of the art. If for example one would try to clone a 27 kb PCR product in a 6.5 kb cosmid a 33.5 kb molecule would result; this would however be too small for lambda packaging.

SUMMARY OF THE INVENTION

Therefore a subject matter of the invention are cosmid vectors of a minimum size of 15 kb and a maximum size of 35 kb. According to the invention they preferably have a size from 15 kb to 32.6 kb. Such vectors are suitable for cloning of DNA fragments of 5 kb to 40 kb. In particular such vectors are suitable for efficient cloning of DNA fragments of a size ranging from 5 kb to 37 kb.

The vectors necessarily contain cos sequences of the lambda bacteriophage, a prokaryotic replication origin, preferably a ColE 1 replica and a gene for selection in antibiotic culture medium, preferably an ampicillin resistance gene. These vectors may additionally contain a cloning cassette. This cassette has one or several sites for any restriction enzyme as well as optionally flanking sequences which may serve as a binding site for universal sequencing primers. In addition these flanking sequences may contain bacteriophage promotors such as SP6, T7 or T3 promoters intended for in vitro transcription of the fragment to be cloned. A subject matter of the invention therefore particularly is a cosmid of the size category mentioned, a part of which is similar to the complete sequence of pHC 79.

According to the invention the sequences used for construction of a cosmid with a size between 15 kb and 35 kb are not selected at will. If usually heterologous DNA fragments are inserted in plasmids of this size category this may often lead to deletion events and/or recombination events between the vector DNA, in particular between the spacer DNA cloned in the plasmid/cosmid, and the fragment to be inserted so that cloning becomes impossible or inefficient.

One cloning version of DNA fragments of eucaryotic origin are cosmids with spacers having sequences of non-eucaryotic origin. A preferred version of the novel vectors are such cosmids containing, apart from the cos sequences as spacers, an additional DNA fragment from the genome of the bacteriophage lambda. This may for example code for structure proteins of the bacteriophage. Since according to the invention these cosmids are also suitable for cloning of PCR fragments, which can be produced with the "Expand" Long Template PCR System, they are called expand vectors in the following.

Particularly preferred are cosmid vectors with an additionally contained DNA fragment consisting either of the 8.5 kb BamHI/Bc1I-fragment (expand vector III), or the 16.8 kb BamHI fragment (expand vector II) or the 25.9 kb BbrI/BspLU1 I fragment (expand vector I) of the bacteriophage lambda cI857Sam7 (Weigle, J. et al. (1966); Proc. Nat. Acad. Sci., U.S.A. 55, 1462–1466). Surprisingly, the presence of such lambda sequences in the cosmid does not lead to interactions with the packaging system during in vitro packaging. Lytic lambda functions are completely switched off, too.

A further subject matter of the invention are Escherichia coli host cells containing one of the vectors described and which are therefore suitable for its replication.

A further subject matter of the invention is the use of the cosmid vectors described for cloning of DNA fragments of a size ranging from 5 kb to 40 kb, preferably of fragments between 7 kb and 36 kb and particularly preferably between 16.5 kb and 25 kb. Fragments to be cloned of this size are for example PCR amplification products which may preferably be produced with the "Expand" PCR System (Boehringer Mannheim, catalogue No. 1681834; 681842; 1759060; 1811002). The size range of DNA fragments directly depends on the size of the cosmid according to the invention. The following table 1 is a survey of the cloning capacity of three vectors constructed according to the invention. The three E. coli strains BMTU 7337 (DSM No. 11839), BMTU 7338 (DSM No. 11840) and BMTU 7339 (DSM No. 11841) containing the expand vectors I, II and III were deposited with the German collection of microorganisms and cell cultures (DSM GmbH), Marschroder Weg 1b, 38124 Braunschweig.

TABLE 1

Expand vector data

|  | Size | Spacer | Cloning capacity |
|---|---|---|---|
| Vector I | 32.6 kb | 25.9 kb | 7.0–16.5 kb |
| Vector II | 23.5 kb | 16.8 kb | 16.5–25.0 kb |
| Vector III | 15.2 kb | 8.5 kb | 25.0–36.0 kb |

A further subject matter of the invention are methods for cloning of DNA fragments in cosmid vectors with the characteristics disclosed where fragments ranging from 5 kb to 40 kb, preferably from 7 kb to 36 kb and particularly preferably from 16.5 kb to 25 kb are cloned. Particularly preferred are PCR amplification products as obtainable by the "Expand" PCR System (Boehringer Mannheim).

Furthermore, a subject matter of the invention is a method for preserving an Escherichia coli suspension in a 5–20 mM $MgSO_4$ solution, preferably a suspension of the DH5alpha strain where the suspension temperature of less than 30° C. but higher than 4° C. is cooled down to −70° C. within a period of more than 30 minutes. Preferably, the suspension is cooled from room temperature to −70° C. within a period of more than 30 minutes. Bacteria treated like this can be used as host organisms for replication of in vitro packaged cosmid DNA without any further pretreatment.

A subject matter of the invention is also a kit for cloning of heterologous DNA containing at least one of the cosmid vectors described. The vector can be linearized and dephosphorylated. The kit may additionally contain one or several enzymes such as DNA ligase, polynucleotide kinase or T4 DNA polymerase. Further optional components of the kit are a lambda in vitro DNA packaging extract and a suspension of E. coli DH5alpha in 5–20 mM $MgSO_4$ solution.

In all Figures. Bold corresponds to the coordinates of the expand vectors, italics corresponds to the coordinates of the lambda genome, the remaining numbers correspond to the coordinates of the pHC79 cosmid.

DETAILED DESCRIPTION OF THE INVENTION

Construction of the Expand Vectors I, II and III:

Expand vector I

Figure 1:
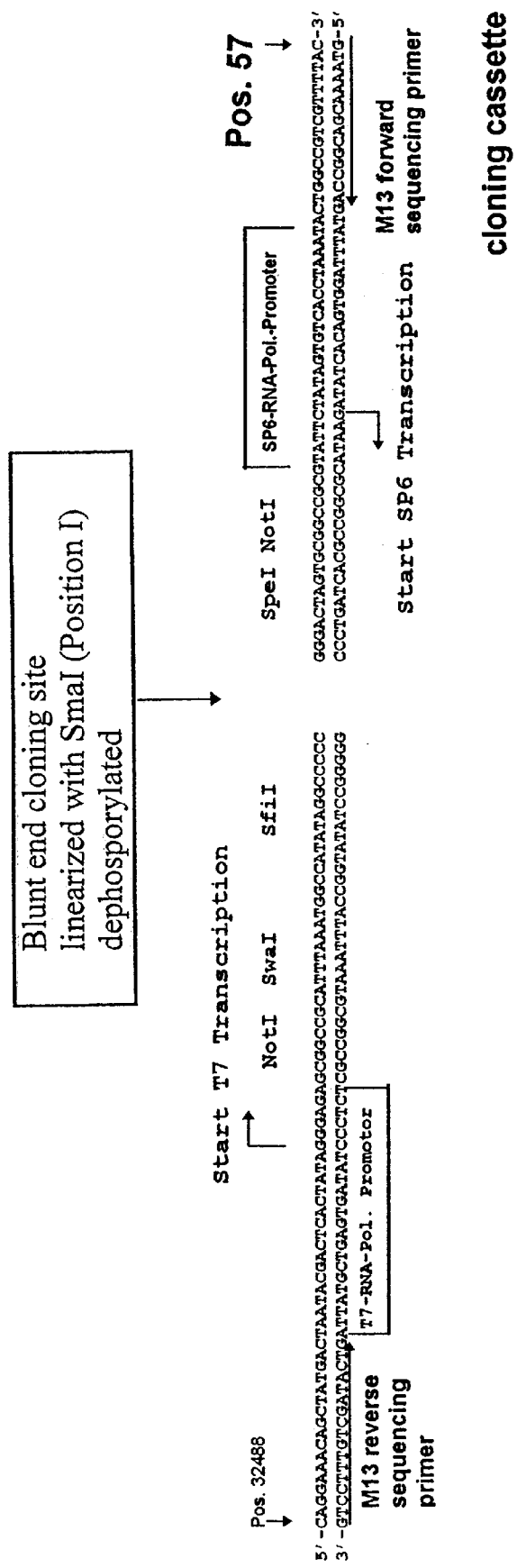
FIG. 1: Cloning cassette which had been inserted in the expand vectors. Fragments to be cloned are inserted in the singular SmaI site (SEQ. ID. No.1).
Figure 2:
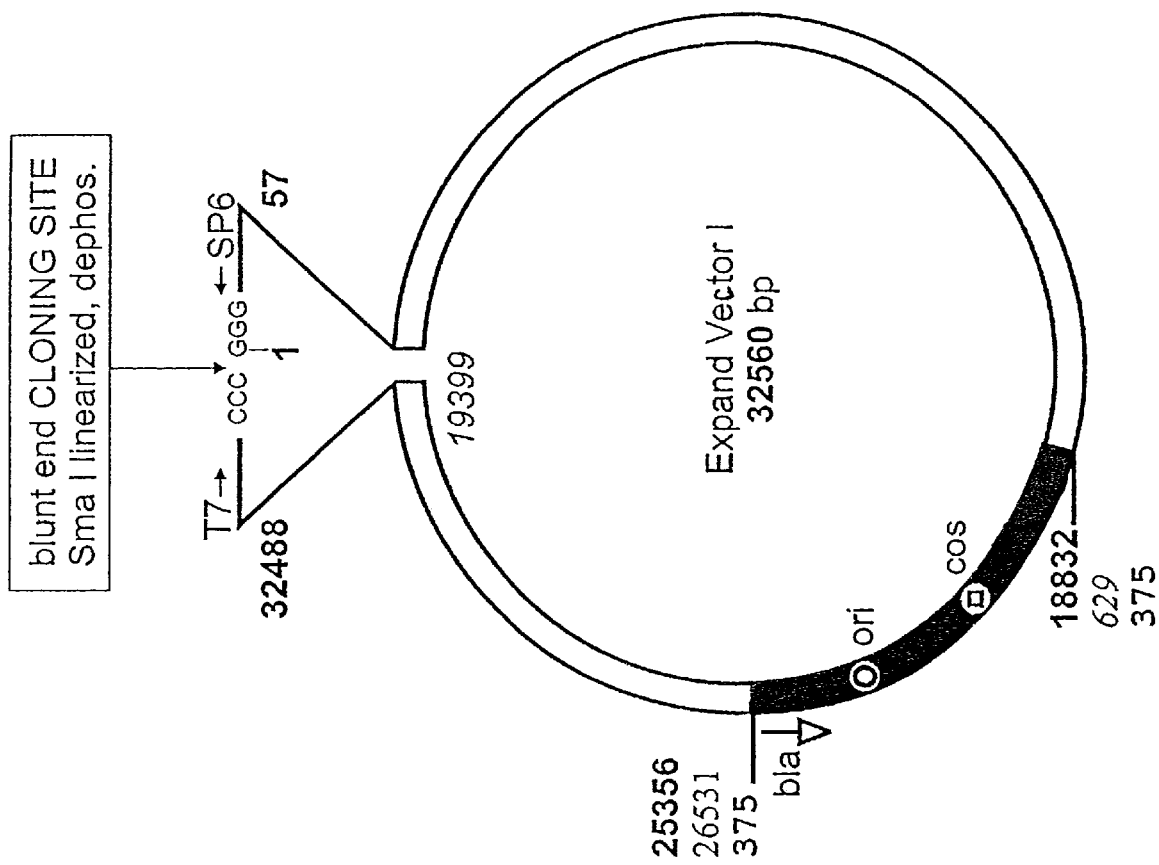
FIG. 2: Expand vector I, 32.6 kb, for cloning of fragments between 7.0 and 16.5 kb

The pHC 79 cosmid was linearized with Bam HI. The resulting 5' overhanging ends were filled with T4 DNA polymerase. To increase the cosmid vector a DNA section from the genomne of the bacteriophage lambda cI 857 Sam7 was cloned as a spacer fragment in the linearized blunt end cosmid. For this, the lambda DNA was cut with the restriction enzymes Bbr I and Bsp LU11 I. The resulting fragment of 25903 bp was separated from the remaining fragments by agarose gel electrophoresis and isolated from the gel. The overhanging ends produced by the above cleavage were filled with T4 DNA polymerase. The resulting lambda DNA fragment (spacer) was ligated in the filled BamHI restriction site of the cosmid described above. After transformation in the bacteria strains E. coli XL I blue the cosmid DNA was isolated and linearized with Sma I. In this cosmid a cloning cassette (FIG. 1, SEQ. ID. No.1) with a length of 129 base pairs (obtained by ligation from 4 synthetic oligonucleotides) was ligated. This cassette contains restriction sites for the rare-cutter restriction enzymes NotI, SwaI, SfiI and SpeI, sequencing primer sequences as well as Sp6/T7 promotors (FIG. 2). The SmaI site (position I) in the middle of the cloning cassette is uniquely present on the expand vectors since the Sma I sites used for cloning of the cassette into the starting plasmid are not regenerated. For this reason the fragments to be cloned are inserted in this SmaI site.

With this construction the expand vector I has a size of 32.5 kb, a lambda spacer of 25.9 kb and a cloning capacity (for the lambda packaging system) of 7.0 to 16.5 kb. This results in a total size from 39.5 to 49 kb and corresponds to a size category which can be packed in the lambda packaging system (FIG. 2).

Expand vectors II and III

Figure 3:
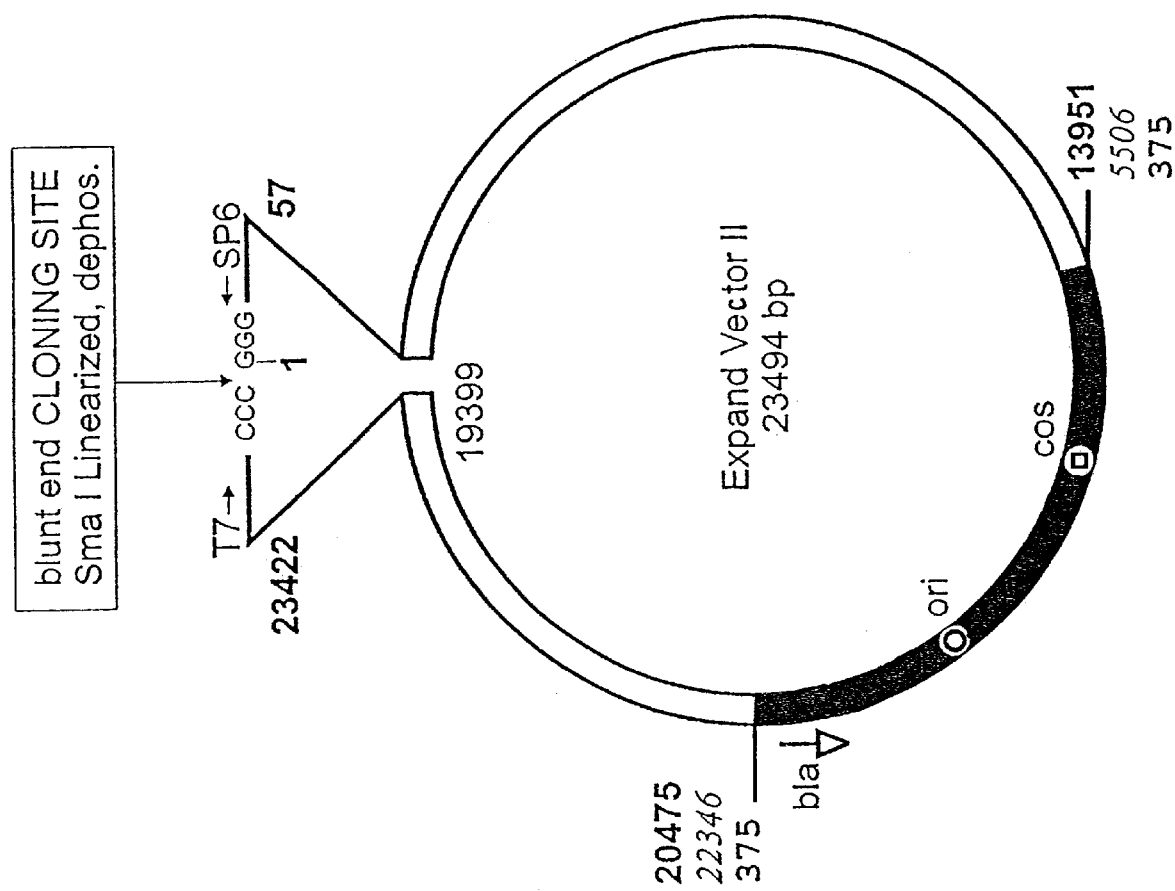
FIG. 3: Expand vector II, 23.5 kb, for cloning of fragments between 16.5 and 25.0 kb
Figure 4:
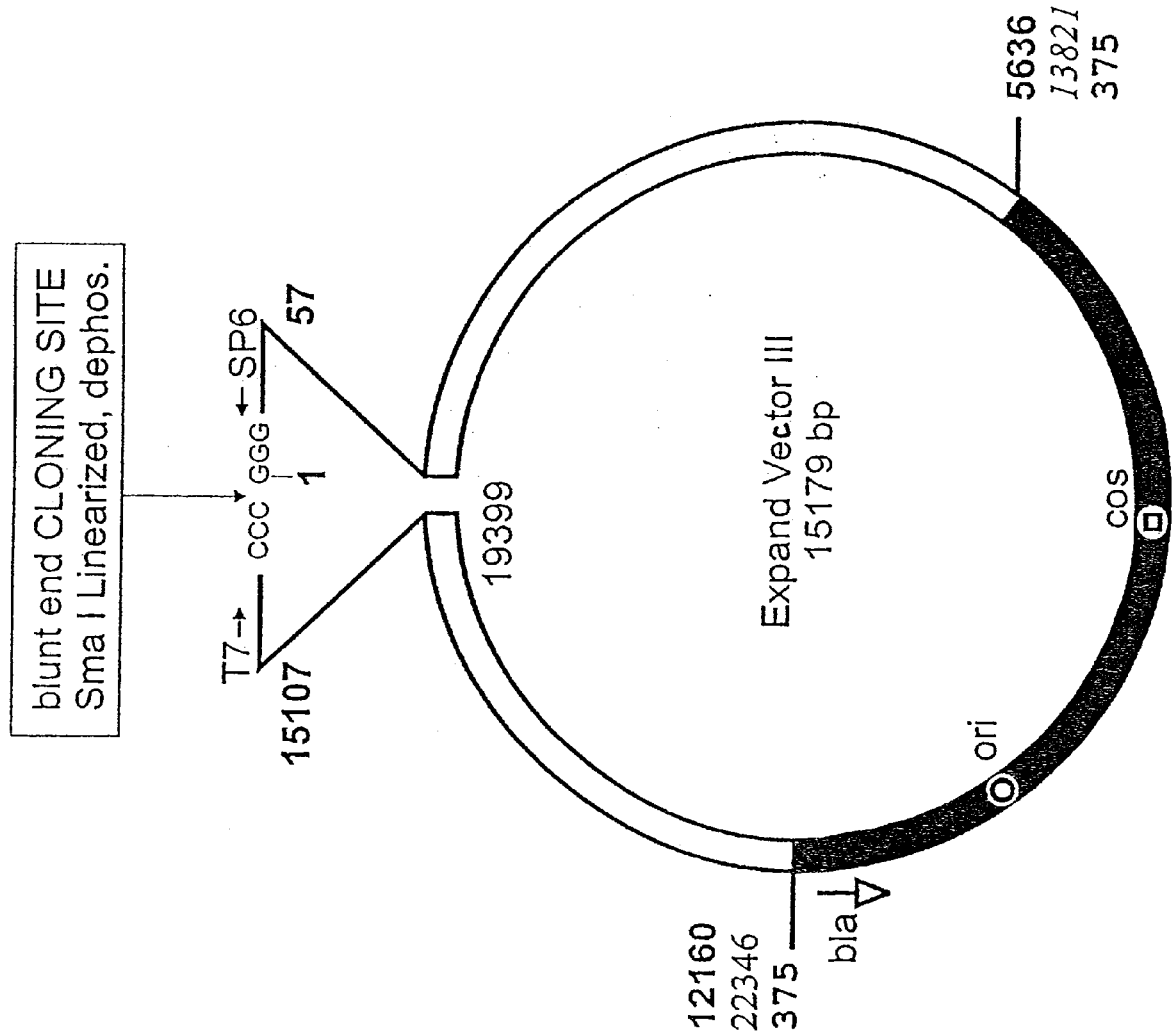
FIG. 4: Expand vector III, 15.2 kb, for cloning of fragments between 25.0 and 36.0 kb.

The construction of the expand vectors II and III is basically analogous to the expand vector I construction. But in the case of the expand vector II a 16841 bp BamH1 fragment was isolated from lambda and directly inserted in the Bam HI site of the cosmid pHC 79. In the case of the expand vector III DNA of the bacteriophage lambda cI 857 Sam7 was cut with Bam HI/Bcl I. Subsequently, a fragment of 8526 bp was isolated and directly inserted in the bam HI site of the pHC 79 cosmid. The insertion of the cloning cassette in the expand vectors II and III was performed exactly according to that of the expand vector I construction (FIGS. 3 and 4). With the insertion of the lambda spacers in pHC 79 cosmid vectors of 23.5 kb and 15.2 kb could be produced. They have a cloning capacity of 16.5 kb–25 kb and 25–36 kb respectively and can be packaged with a lambda packaging extract.

Thus the use of one of the expand vectors I, II or III allows the cloning of fragments of the size category 7 to 36 kb. By this, DNA fragments of a certain size category which before had been too large to be cloned with conventional plasmids and too small to be cloned with cosmids can now be cloned.

The invention is further described in the following examples:

EXAMPLE 1

Cloning of a 23.3 kb PCR fragment

From human genomic DNA a 23.3 kb PCR fragment from the β-globin gene region was amplified by specific primers. For this a commercially available kit ("Expand" 20 kb$^{Plus}$ PCR System, Boehringer Mannheim, catalogue No. 1681834) was used. This kit contains a special enzyme mixture of Taq DNA polymerase, Pwo DNA polymerase and one further heat resistant enzyme.

The primers used for PCR have the following sequences:

Forward primer: 5'CACAAGGGCTACTGGTTGC-CGATT3' (SEQ. ID. No. 2)

Reverse primer: 5'AGCTTCCCAACGTGATCGCCTT3' (SEQ. ID. No. 3)

PCR conditions:

250 ng human genomic DNA
400 nmol primer (forward; reverse)
0.5 mmol dNTPs
10 µl 5x "EXPAND" 20 kb$^{plus}$ buffer
0.75 µl "EXPAND" 20 kb$^{plus}$ enyme mixture
filled up with bidist. water to a quantity of 50 µl.

Cycle conditions:

2 min. at 92° C.
10 cycles of:   10 sec. at 92° C.
                30 sec. at 62° C.
                18 sec. at 68° C.
20 cycles of:   10 sec. at 92° C.
                30 sec. at 62° C.
                18 sec. at 68° C.
+ cycle prolongation of 20 sec. for each cycle
7 min. at 68° C.

After amplification the PCR fragments were analyzed by gel electrophoresis and then purified with the High Pure PCR Template Preparation Kit (Boehringer Mannheim catalogue No. 1796828). Subsequently, the PCR fragments were modified by a polishing reaction (production of blunt ends) and a phosphorylation reaction (addition of 5' phosphates since unphosphorylated primers were used): For the modification reaction 1 µg of purified 23.3 kb PCR fragment (which corresponds to the yield of a 50 µl PCR reaction) was used. The polishing and phosphorylation reactions were performed in a "one tube" reaction as follows: 8 µl 5×T4 DNA polymerase buffer+dNTP, 4 µl 10×phosphorylation buffer+ATP, 1 U T4 DNA polymerase (Boehringer Mannheim catalogue No. 1004786) and 10 U T4 polynucleotide kinase (Boehringer Mannheim catalogue No. 174645) are added to the PCR fragment. The preparation is then filled up to 40 µl with bidistilled water and then incubated at 37° C. for 20 minutes. After the reaction the modified PCR fragments are purified with the High Pure PCR Template Preparation Kit (Boehringer Mannheim catalogue No. 1796828).

The expand vector II was linearized with SmaI and then dephosphorylated with alkaline phosphatase. For the ligation with 100 ng of the expand vector II 200 ng linearized 23.3 kb expand PCR fragment was used (twice molar excess). After adding 10 µl 2×ligation buffer$^{plus}$ and 5 U T4 DNA ligase (Boehringer Mannheim catalogue No. 799009) the preparation was filled up to 20 µl with bidistilled water and incubated for 30 min. at room temperature (22° C.) and for at least 5 min. at −70° C. Compared to an unfrozen ligation reaction this freezing reaction at −70° C. leads to a 2–4 fold increase in the number of bacteria colonies.

For the subsequent packaging reaction with the DNA Packaging Kit 5 µl of the ligation preparation were added to 25 µl DNA packaging extract (Single Tube System, Boehringer Mannheim catalogue No. 1758772) and incubated for 2 hours at room temperature (22° C.). The packaging reaction was stopped by addition of 50 µl SM-buffer (50 mmol Tris/HCl, pH7.5/22° C.; 10 mM MgSO$_4$; 100 mM NaCl; 0.01% gelatine) and 20 µl chloroform.

To infect the bacteria cells with the phage supernatant an E. coli magnesium culture was prepared in 10 mM magnesium sulfate (Hohn, T. Gene 11, 291–298, 1980). For this, the E.coli strain DH5 α was bred up to an OD$_{600}$ of 1.0 in LB medium under addition of maltose and magnesium sulfate (0.2% maltose; 10 mM. MgSO$_4$). After centrifugation the bacteria pellet was resuspended in an appropriate volume of 10 mM MgSO$_4$ so that an OD$_{600}$ of 1.0 was obtained. 50 µl of this E. coli magnesium culture were incubated with 25 µl of phage supernatant (2 volumes of magnesium culture, 1 volume of phage supernatant) for 30 minutes at room temperature (22° C.). Generally it is however also possible to incubate up to 500 µl of the magnesium culture with up to 250 µl of phage supernatant as long as the volume ratio is 2:1. After adding 100–1000 µl LB medium and incubating for 60 min. at 37° C. the infected bacteria cells were plated on L]3 plates with ampicillin (100 µg/ml) and incubated over night at 37° C.

With this experiment 132 bacteria colonies could be obtained on one agar plate. The resulting clones were agitated in LB medium with ampicillin (100 µg/ml) over night at 37° C. The cosmid DNA was isolated according to standard methods (Maniatis et al. Molecular Cloning. A Laboratory Manual, Cold Spring Harbour, Laboratory Press, Cold Spring Harbour, N.Y. 1982) and analyzed by restriction cleavage with Not I/Bln I. 46 (92%) out of 50 clones analyzed by cleavage with restriction enzymes were positive, i.e. they contained the PCR fragment (23.3 kb) to be cloned which had the correct size and the restriction pattern to be expected.

EXAMPLE 2

Cloning of a DNA Fragment with Overhanging Ends

An SPP I phage fragment of 8576 base pairs obtained by cleavage with Eco RI was polished (to obtain blunt ends) after fractionation by agarose gel electrophoresis and isolation from the gel (concentration: 500 ng in 20 μl) by adding 8 μl 5×T4 DNA polymerase buffer and 1 U T4 DNA polymerase in a final volume of 40 μl (filling up with bidist. water) by incubation at 37° C. for 20 minutes. Subsequently, the DNA fragment was purified with High Pure PCR Template Preparation Kit (Boehringer Mannheim) and then ligated in the expand vector I (twice the molar insert excess compared to the vector) linearized with Smal and dephosphorylated with alkaline phosphatase. As in example 1 5 μl (a quarter) of the ligation reaction was added to 25 μl of DNA Packaging Extract (Single Tube System, Boehringer Mannheim catalogue No. 1758772), plated on LB plates with ampicillin (150 μg/ml) and bred at 37° C. over night after incubation at room temperature (22° C.) for 2 hours and incubation with a magnesium culture of the E. coli DH5α strain. The clones received (230) were bred in 10 ml LB medium with ampicillin (150 μg/ml) over night at 37° C. The cosmid DNA was isolated according to standard methods (Maniatis et al. 1982, supra) and analyzed by restriction cleavage with Not I and Not I/Eco RI. 27 out of 30 clones analyzed contained the insert (90%) showing the correct size and restriction pattern to be expected.

The high cloning frequence of 90% and 92% respectively, which could be received in both examples, proves that the expand vectors according to the invention are suitable for cloning of particularly large fragments since recombination events with the comparatively large vector DNA and deletion events do obviously not occur or occur only very rarely in the cloned inserts or the vectors.

What is claimed is:

1. A cosmid vector comprising the complete nucleic acid sequence of pHC79 vector and a DNA fragment selected from the group consisting of the 8.5 kb BamHI/BclI fragment, the 16.8 kb BamHI fragment, and the 25.9 kb BbrI/BspLu 11 fragment of the bacteriophage lambda cI857Sam7; said vector having a maximum size of 35 kb.

2. An *Escherichia coli* host cell containing the cosmid vector of claim 1.

3. A method for cloning a DNA fragment of a size between 5 kb and 40 kb comprising ligating said DNA fragment to a linearized cosmid vector of claim 1.

4. A kit containing a cosmid vector of claim 1.

5. A kit of claim 4, additionally containing a lambda DNA packaging extract.

6. A kit of claim 5, additionally containing a suspension of DH5alpha in MgSO$_4$ solution.

7. A method for the preservation of an *Escherichia coli* suspension in 5–20 mM MgSO$_4$ solution, comprising cooling said suspension from a temperature less than 30° C. but higher than 4° C. to −70° C. over a period of at least 30 minutes.

8. A method of replicating an in vitro packaged cosmid DNA, comprising transducing a host *Escherichia coli* with said cosmid DNA, wherein said host *Escherichia coli* has been preserved by the method of claim 7, thereby replicating the packaged cosmid DNA.

* * * * *